(12) United States Patent  (10) Patent No.: US 8,652,118 B2
Peyman  (45) Date of Patent: *Feb. 18, 2014

(54) SUB-MUCOSAL AGENT DELIVERY, APPARATUS, SYSTEM AND METHOD (75) Inventor: Gholam A. Peyman, Sun City, AZ (US)

(73) Assignee: KMG Pharma, LLC, Mountain View, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 12/931,834

(22) Filed: Feb. 10, 2011

(65) Prior Publication Data
US 2011/0251585 A1    Oct. 13, 2011

Related U.S. Application Data (63) Continuation-in-part of application No. 12/931,846, filed on Feb. 10, 2011.

(60) Provisional application No. 61/342,164, filed on Apr. 8, 2010.

(51) Int. Cl.
A61M 31/00    (2006.01)
A61M 35/00    (2006.01)

(52) U.S. Cl.
USPC .................................... 604/521; 604/290

(58) Field of Classification Search
USPC .......... 604/116, 506, 521, 289, 290, 294–302
See application file for complete search history.

(56) References Cited

U.S. PATENT DOCUMENTS

| 5,505,697 A | 4/1996 | McKinnon, Jr. et al. |
| 5,704,911 A | 1/1998 | Parsons |
| 5,954,689 A | 9/1999 | Poulsen |
| 6,123,684 A * | 9/2000 | Deboer et al. ................ 604/68 |
| 6,309,374 B1 * | 10/2001 | Hecker et al. ............... 604/117 |
| 6,585,685 B2 | 7/2003 | Staylor et al. |
| 6,682,504 B2 | 1/2004 | Nelson et al. |
| 6,746,429 B2 | 6/2004 | Sadowski et al. |

(Continued)

FOREIGN PATENT DOCUMENTS

WO    02/00278 A2    1/2002

OTHER PUBLICATIONS

PCT Form 210, International Search Report for PCT/US2011/000579, mailed on May 25, 2011.

(Continued)

*Primary Examiner* — Bhisma Mehta
*Assistant Examiner* — Bradley Osinski
(74) *Attorney, Agent, or Firm* — The Law Office of Patrick F. O'Reilly, III, LLC (57) ABSTRACT

An agent delivery apparatus for administering a pharmacological agent formulation to a sub-mucosal compartment of a body organ, comprising injector means having an internal formulation chamber that is adapted to receive and contain the pharmacological agent formulation therein and an elongated agent delivery member having a first end that is in communication with the internal formulation chamber and a second ejection end, the injector means including force generating means that is adapted to generate sufficient force to expel the pharmacological agent formulation from the injector means and into and through the agent delivery member, and out of the ejection end of the elongated agent delivery member. In one embodiment of the invention, the delivery member comprises a needleless delivery member.

5 Claims, 3 Drawing Sheets

(56) References Cited

U.S. PATENT DOCUMENTS

| | | | |
|---|---|---|---|
| 7,147,633 B2 * | 12/2006 | Chee et al. | 606/41 |
| 7,150,409 B2 | 12/2006 | Gonnelli et al. | |
| 7,678,078 B1 | 3/2010 | Peyman et al. | |
| 2003/0229308 A1 * | 12/2003 | Tsals et al. | 604/116 |
| 2004/0138621 A1 | 7/2004 | Jahns et al. | |
| 2006/0095079 A1 | 5/2006 | Gerber | |
| 2007/0055200 A1 | 3/2007 | Gilbert | |
| 2007/0055214 A1 * | 3/2007 | Gilbert | 604/500 |
| 2007/0260201 A1 | 11/2007 | Prausnitz et al. | |
| 2008/0058760 A1 | 3/2008 | Agerup | |
| 2009/0018602 A1 * | 1/2009 | Mitelberg et al. | 607/40 |
| 2010/0030150 A1 * | 2/2010 | Paques et al. | 604/116 |
| 2011/0251578 A1 | 10/2011 | Peyman | |
| 2011/0251586 A1 | 10/2011 | Peyman et al. | |

OTHER PUBLICATIONS

PCT Form 237, Written Opinion of the International Searching Authority for PCT/US20111000579, mailed on May 25, 2011.

PCT Form 373, International Preliminary Report on Patentability for PCT/US2011/00579, date of issuance of report: Oct. 9, 2012.

PCT Form 210, International Search Report for PCT/US2011/000580, mailed on May 23, 2011.

PCT Form 237, Written Opinion of the International Searching Authority for PCT/US20111000580, mailed on May 23, 2011.

PCT Form 373, International Preliminary Report on Patentability for PCT/US2011/00580, date of issuance of report: Oct. 9, 2012.

First office action on the merits (Non-Final Rejection) in U.S. Appl. No. 12/931,846, mailed on Jul. 12, 2012.

Second office action on the merits (Final Rejection) in U.S. Appl. No. 12/931,846, mailed on Oct. 15, 2012.

First office action on the merits (Non-Final Rejection) in U.S. Appl. No. 12/932,941, mailed on Jul. 5, 2012.

Second office action on the merits (Final Rejection) in U.S. Appl. No. 12/932,941, mailed on Oct. 15, 2012.

Third office action on the merits (Non-Final Rejection) in U.S. Appl. No. 12/931,846, mailed on Mar. 4, 2013.

* cited by examiner

SUB-MUCOSAL AGENT DELIVERY, APPARATUS, SYSTEM AND METHOD

CROSS-REFERENCE TO RELATED APPLICATIONS

This application is a continuation-in-part of U.S. application Ser. No. 12/931,846 filed Feb. 10, 2011, which claims the benefit of U.S. Provisional Application No. 61/342,164, filed Apr. 8, 2010.

FIELD OF THE INVENTION

This invention relates generally to trans-mucosal agent delivery as a means of treating various conditions affecting mucosa and sub-mucosa of an organ, such as the eye, nose, mouth, throat, trachea, esophagus, stomach, urethra, bladder and vagina. More particularly, the invention relates to improved means for performing mucosa and sub-mucosal agent delivery with the benefits of improved safety for the patient and increased efficiency for the practitioner.

BACKGROUND OF THE INVENTION

As is well known in the art, delivery of pharmacological agents (or drugs) to a specific organ or tissue can be achieved through systemic or local administration. In systemic administration, the agent is introduced into the systemic, or general, circulation by ingestion, injection, inhalation and trans-dermal or trans-mucosal administration by local application of drops or ointments. Circulating blood delivers the agent to the target tissue by either passive or active transport.

Advantages of systemic administration are that this mode of administration, especially by ingestion, is simple and well accepted by the patient. A disadvantage, however, is that the agent must be administered at relatively high doses in order to reach the target area in sufficient quantity. Moreover, the agent is delivered to the entire body, which can include sites where the agent can cause significant side effects. This is especially true for chemotherapeutic agents that tend to present significant systemic toxicity, and steroids, which present significant long-term systemic side effects.

Another significant disadvantage of systemic administration is that transfer of many pharmacological agents from the blood to certain tissues, such as the brain or an eye, is very inefficient.

An alternative to systemic administration is to administer the pharmacological agent(s) into a target organ (or tissue) or in close proximity thereto. However, as is well known in the art, local administration of an agent into or proximate an organ; particularly, an eye, typically requires strict adherence to numerous safeguards.

As discussed in detail herein, the eye is a delicate and complex sense organ that is surrounded by specialized structures and protected by the orbit bones, soft tissues and eyelids. Because of the complex nature of the eye, it is susceptible to a large number of abnormalities (and/or diseases). The abnormalities include dry eye, allergies, infections, various inflammatory diseases and glaucoma.

Treatments of the abnormalities and diseases have, in general, been limited to topical administration of agents or preparations. A conventional example of topical administration of an agent to the eye is the delivery of timolol via eye drops.

As is well known in the art, eye drops facilitate transmission of the agent directly to the anterior part of the eye by instillation of the agent into the cul-de-sac. The agents are then moved via the tears of the eye across the cornea and sclera into the anterior and posterior chambers of the eye without initially entering the systemic circulation path.

The advantage of this mode of administration (or delivery) is that the agent is concentrated in the target tissue with a much lower systemic exposure. This tends to reduce the above-mentioned systemic effects.

A disadvantage of this mode of administration is that not all eye tissues are accessible by this route of delivery. Tears can also redirect a significant portion of the agent away from the target area relatively quickly.

A further disadvantage of this mode of administration is that it is mostly applicable to small molecular weight pharmacological agents. Indeed, large molecular weight agents, such as antibodies, are known to diffuse poorly across the cornea or the sclera.

Although jet injection devices have been employed for injecting pharmacological agents or medication inside the eye, there are no known references disclosing trans-mucosal delivery of pharmacological agents into the sub-mucosal spaces in the eye, mouth, nose, throat, esophagus, urethra, bladder or vagina.

Further, even when jet injection devices are employed to administer pharmacological agents or medication inside the eye, there are several drawbacks and disadvantages associated therewith. A significant disadvantage is that the conventional jet injection devices do not include a transfer mechanism that is adapted to provide safe, accurate, consistent and rapid delivery of pharmacological agents into the eye; particularly, a sub-mucosal compartment in the eye.

Further significant disadvantages are (i) the conventional jet injection transfer mechanism typically include a rigid, substantially linear delivery member, which in many instances restricts access into a sub-mucosal compartment, and (ii) the jet injection devices do not include any means of ensuring perpendicular placement of the surface of an organ, e.g., eye, which is an important factor to achieve effective agent delivery to an organ's mucosa.

Sub-mucosal injection using a conventional needle is also painful and each injection requires several steps to prepare the eye and safely perform the injection. The time required to perform injections can thus disrupt office schedules, resulting in unexpected prolongation of patient waiting times.

Associated with the development of new pharmacological treatments for retinal corneal, glaucoma, ENT, gum, urethra, bladder, vaginal and other diseases, specialists are being faced with the responsibility for meeting the ever increasing demand for delivery of pharmacological agents to an organ; particularly, an organ's mucosa and/or sub-mucosal compartment. Several devices and techniques, such as topical application of pharmacological agents on the mucosa, to delivery pharmacological agents to an organ have thus been employed. There are, however, similarly several drawbacks and disadvantages associated with this mode of administration.

By way of example, it is well known in the art that topical application of pharmacological agents on the mucosa is, in many instance, not very effective since the agent has a limited efficacy period, i.e. will generally not last for a long period of time. Slow release pharmacological agents, such as nanoparticles, microspheres and liposome, similarly have a limited efficacy period.

It would therefore be desirous to provide an improved agent delivery apparatus and associated method to standardize and simplify the sub-mucosal agent delivery process, improve patient comfort and safety, and increase efficiency of the process.

It is therefore an object of the present invention to provide an agent delivery method and system that provides safe, accurate, consistent, and rapid delivery of pharmacological or therapeutic agents into the sub-mucosal compartment of organs.

It is another object of the present invention to provide a sub-mucosal agent delivery method and system that facilitates minimally invasive delivery of therapeutic agents into the sub-mucosal compartment of organs with minimal risk of trauma and infection.

It is another object of the present invention to a sub-mucosal agent delivery method and system that facilitates delivery of therapeutic agents into the subconjunctival, retrobulbar, subtenon, intrascleral and subchoroidal compartments of the eye and/or behind the lid thereof.

SUMMARY OF THE INVENTION

In accordance with the above objects and those that will be mentioned and will become apparent below, in one embodiment of the invention, there is disclosed an agent delivery apparatus for administering a pharmacological agent formulation to a sub-mucosal compartment of a body organ, comprising injector means having an internal formulation chamber that is adapted to receive and contain the pharmacological agent formulation therein and an elongated agent delivery member having a first end that is in communication with the internal formulation chamber and a second ejection end, the injector means including force generating means that is adapted to generate sufficient force to expel the pharmacological agent formulation from the injector means and into and through the agent delivery member, and out of the ejection end of the elongated agent delivery member.

In one embodiment of the invention, the agent delivery member comprises a needleless agent delivery member.

In one embodiment of the invention, the agent delivery member comprises a microneedle agent delivery member.

In one embodiment of the invention, the injector means provides a delivery pressure in the range of approximately 50-1000 psi.

In one embodiment, the agent delivery member is fabricated with a fixed curvature and arch providing access to certain organ's mucosa.

In one embodiment, the agent delivery member is fabricated using a flexible material that would allow an operator to bend the delivery member to a desirable orientation to facilitate agent delivery to an organ's mucosa and its particular location.

In one embodiment of the invention, the agent delivery member includes a hood.

In some aspects of the invention, the hood comprises a positioning hood that is adapted to substantially conform to the surface of an organ and position the delivery member on the organ when in an engagement position thereon.

In some aspects of the invention, the hood is further adapted to slightly retract when in contact with the organ's surface to permit positioning of the hood in an angulated space, such as a retrobulbar space or behind the lid of an eye.

In some aspects of the invention, the hood comprises microneedle limiter means for limiting the penetration depth of a microneedle associated with a microneedle agent delivery member.

In one embodiment of the invention, the hood includes suction means that provides an engagement force when the hood is positioned on an organ's surface.

In one embodiment of the invention, the injector means includes a formulation cartridge, such as those disclosed in Applicant's U.S. Pat. No. 7,678,078, which is adapted to contain the pharmacological agent formulation.

In another embodiment, the injector means includes multiple cartridges adapted to receive multiple pharmacological agent formulations for delivery.

In accordance with another embodiment of the invention, there is disclosed a method for administering a pharmacological agent formulation to a sub-mucosal compartment of a body organ, comprising the steps of (i) providing an agent delivery apparatus having the pharmacological agent formulation contained in an internal formulation chamber, the agent delivery member including an elongated agent delivery member having a first end that is in communication with the internal formulation chamber and a second ejection end, the injector means including force generating means that is adapted to generate sufficient force to expel the pharmacological agent formulation from the injector means and into and through the agent delivery member, and out of the ejection end of the elongated agent delivery member, (ii) positioning the agent delivery apparatus proximate a mucosal layer associated with the body organ, and (iii) activating the agent delivery apparatus, whereby the pharmacological agent formulation is expelled from the agent delivery apparatus and into a sub-mucosal compartment of the body organ.

In one embodiment of the invention, the agent delivery apparatus provides an agent delivery pressure in the range of approximately 50-1000 psi.

In one embodiment of the invention, the volume of the pharmacological agent formulation delivered to the sub-mucosal compartment is in the range of approximately 0.025-2 ml.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENTS

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that, although the agent delivery apparatus, systems and methods of the invention are illustrated and described in connection with delivery of a pharmacological agent formulation to the mucosa and/or a sub-mucosa compartment of an eye, the agent delivery apparatus, systems and methods of the invention are not limited to such delivery. According to the invention, the agent delivery apparatus, systems and methods of the invention can be readily employed to effectuate delivery of a pharmacological agent formulation to the mucosa and/or a sub-mucosa compartment of a body organ, including, without limitation, the nose, mouth, throat, trachea, esophagus, stomach, urethra, bladder and vagina.

It is further to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise. Thus, for example, reference to "pharmacological agents" includes two or more such agents and the like.

DEFINITIONS

The term "mucosa," as used herein, means and includes the inner layer of any epithelially-lined hollow organ, such as the eye, nose, mouth, throat, trachea, esophagus, stomach, urethra, bladder and vagina.

The terms "therapeutic agent," "pharmacological agents," "pharmaceutical agent," "agent," "active agent," and "pharmaceutical composition" are used interchangeably herein and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active agent that can be delivered includes inorganic and organic compounds.

According to the invention, suitable active agents can be selected from, for example, small molecules, such as steroids and NSAIDs, proteins, enzymes, hormones, oligonucleotides, polynucleotides, nucleoproteins, modified DNA and RNA loaded viruses with modified capsid, polysaccharides, glycoproteins, lipoproteins, polypeptides, including drug carriers, such as pokymers, micro and nano particles.

Further examples of active agents useful in this invention include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, bupivacaine, ropivacaine, dibucaine, etidocaine, tetracaine, lidocaine, xylocaine, procaine, chloroprocaine, prilocaine, mepivacaine, oxybuprocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3. NT-4, NGF, IGF-2, anti-VEGF's, anti-PDGF's, growth factors, Botulinum toxin, antibiotics or antifungal drugs, anti pain medication, anesthetics, and combinations thereof, and salts thereof.

It is to be understood that more than one active agent can be combined or mixed together and incorporated into or used by the present invention, and that the use of the term "pharmacological agent," "pharmaceutical agent," "agent," "active agent," or "pharmaceutical composition" in no way excludes the use of two or more such "pharmacological agents," "pharmaceutical agents," "agents," "active agents," and "pharmaceutical compositions."

The terms "active agent formulation," "pharmacological agent formulation," and "formulation", as used herein, mean and includes an active agent optionally in combination with one or more pharmaceutically acceptable carriers and/or additional inert ingredients. According to the invention, the formulation can be either in solution or in suspension (such as nanoparticles, microspheres or liposomes) in the carrier. The active agent can be formulated as an immediate release or a delayed release or a slow release formulation.

As used in this application, the term distal shall mean the end or direction toward the front of a jet injector. The term proximal shall mean the end or direction toward the rear of the injector.

As discussed in detail herein, the present invention is directed to novel agent delivery devices, their methods of manufacture and their methods of use. The invention also provides improved means of performing sub-mucosal agent delivery to a body organ with the benefits of improved safety for the patient and increased efficiency for the practitioner.

It is again emphasized that, although the agent delivery apparatus, systems and methods of the invention are illustrated and described in connection with delivery of a pharmacological agent formulation to the mucosa and/or a sub-mucosa compartment of an eye, the agent delivery apparatus, systems and methods of the invention are not limited to such delivery. According to the invention, the agent delivery apparatus, systems and methods of the invention can be readily employed to effectuate delivery of a pharmacological agent formulation to the mucosa and/or a sub-mucosa compartment of any body organ, including, without limitation, the nose, mouth, throat, trachea, esophagus, stomach, urethra, bladder and vagina.

Figure 1:
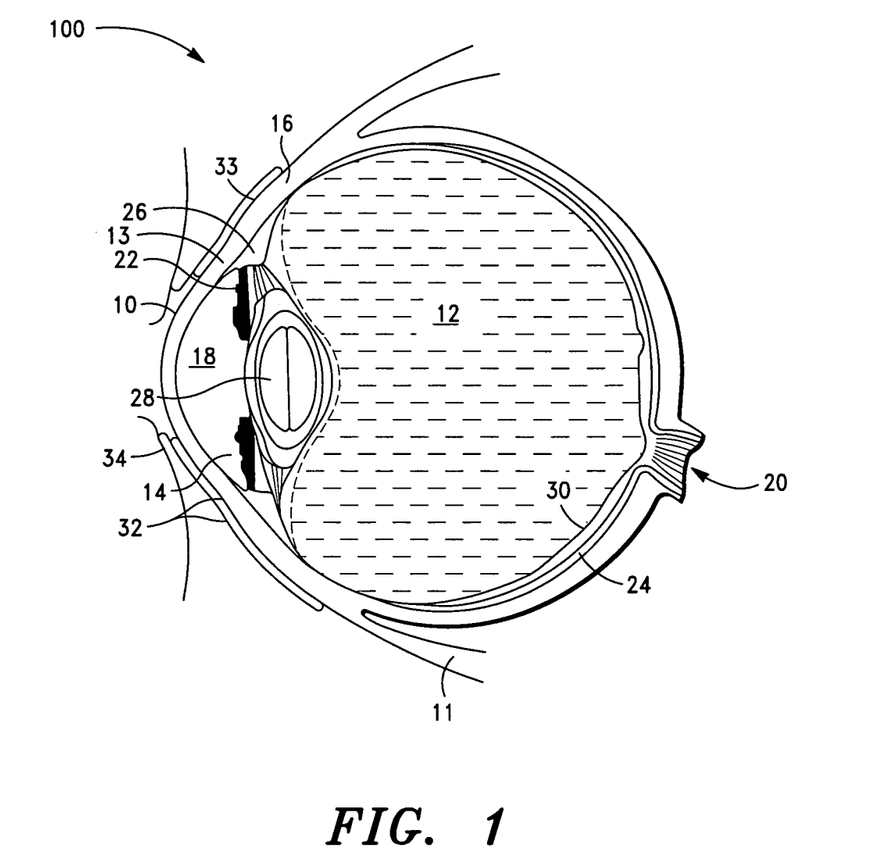
FIG. 1 is a schematic illustration of a human eye.

The following is a brief description of the key anatomical components of the eye, which will help in the understanding of the various features of the invention:

Referring to FIG. 1, the cornea 10 is the transparent window that covers the front of the eye 100. The cornea 10 is a lens-like structure that provides two-thirds of the focusing power of the eye 100.

The cornea 10 is slightly oval and has an average diameter of about 12 mm horizontally and 11 mm vertically. The central thickness of the cornea 10 is approximately 0.5 mm and approximately 1 mm thick at the periphery.

The sclera 16 is the white region of the eye 100, i.e. posterior five sixths of the globe. The sclera 16 is the tough, avascular, outer fibrous layer of the eye that forms a protective envelope. The sclera 16 is mostly composed of dense collagen fibrils that are irregular in size and arrangement (as opposed to the cornea).

The sclera 16 can be subdivided into three (3) layers: the episclera, sclera proper and lamina fusca. The episclera is the most external layer. The episclera is a loose connective tissue adjacent to the periorbital fat and is well vascularized.

The sclera proper, also called tenon's capsule, is the layer that gives the eye its toughness. The sclera proper is avascular and composed of dense type I and III collagen.

The lamina fusca is the inner aspect of the sclera 16. It is located adjacent to the choroid 24 and contains thin collagen fibers and pigment cells.

The pars plana is a discrete area of the sclera 16. This area is a virtually concentric ring that is located between 2 mm and 4 mm away from the cornea 10.

The mean scleral thickness±SD of the pars plana is reported to be approximately 0.53±0.14 mm at the corneo-scleral limbus, significantly decreasing to 0.39±0.17 mm near the equator, and increasing to 0.9 to 1.0 mm near the optic nerve. At the location of the pars plana, the thickness of the sclera is about 0.47±0.13 mm.

The thickness of the sclera 16 is known to vary according to sex, age, and is altered in various pathological conditions. Overall, the range of thickness of the sclera 16 at the location of the pars plana is estimated to be in the range of approximately 0.3-1.0 mm. The total thickness of the membranes enclosing the eye cavity, at the location of the pars plana, is estimated to be in the range of approximately 0.5-1 mm.

The limbus 13 is the 1-2 mm transition zone between the cornea 10 and the sclera 16. This region contains the outflow apparatus of the aqueous humor 14.

As illustrated in FIG. 1, the extraocular muscles 11 insert into the sclera 16 behind the limbus 13.

The conjunctiva 32 forms a continuous muscosal tissue layer, i.e. a thin clear vascular mucous membrane, which begins at the limbus 13 and covers the sclera 16 and the inner surface of the eyelid 34. The mucosal tissues generally include an epithelial or mucosal epithelial surface overlying a sub-mucosa comprising connective tissue, vessels and nerves.

The conjunctiva 32 generally comprises three (3) sections: (i) the palpebral conjunctiva, which covers the posterior surface of the eyelids, (ii) the bulbar conjunctiva, which coats the anterior portion of the eyeball, and (iii) the formix, which comprises the transition portion; forming the junction between the posterior eyelid and the eyeball.

Within the bulbar conjunctiva are "goblet cells," which secrete the mucin. This is an important component of the pre-corneal tear layer that protects and nourishes the cornea 10.

The average thickness of the conjunctiva 32 is about 0.05 mm. Although the palpebral conjunctiva is moderately thick, the bulbar conjunctiva is very thin.

The subconjunctival compartment or space 33 is the space disposed proximate and under the conjunctiva 32.

The uvea refers to the pigmented layer of the eye 100 and is made up of three (3) distinct structures: the iris 22, ciliary body 26, and choroid 24. The iris 22 is the annular skirt of tissue in the anterior chamber that functions as an aperture. The iris root attaches to the ciliary body 26 peripherally. The pupil is the central opening in the iris 22.

The ciliary body 26 is the 6 mm portion of uvea between the iris 22 and choroid 24. The ciliary body 26 is attached to the sclera 16 at the scleral spur. It is composed of two zones: the anterior 2 mm pars plicata, which contains the ciliary muscle, vessels, and processes, and the posterior 4 mm pars plana.

The ciliary muscle controls accommodation (focusing) of the lens 28, while the ciliary processes suspend the lens (from small fibers called zonules) and produce the aqueous humor (the fluid that fills the anterior and posterior chambers and maintains intraocular pressure).

The choroid 24 is the tissue disposed between the sclera 16 and retina 30. The choroid 24 is attached to the sclera 16 at the optic nerve 20 and scleral spur. This highly vascular tissue supplies nutrients to the retinal pigment epithelium (RPE) and outer retinal layers.

The layers of the choroid 24 (from inner to outer) are: Bruch's membrane, choriocapillaris, and stroma. Bruch's membrane separates the RPE from the choroid 24 and is a permeable layer composed of the basement membrane of each, with collagen and elastic tissues in the middle.

A suprachoroidal space exists between the choroid 24 and sclera 16. In certain disease processes, fluid or blood can fill this space creating a choroidal detachment.

The crystalline lens 28, located between the posterior chamber and the vitreous cavity, separates the anterior and posterior segments of the eye 100. Zonular fibers suspend the lens 28 from the ciliary body 26 and enable the ciliary muscle to focus the lens 28 by changing its shape.

The retina 30 is the delicate transparent light sensing inner layer of the eye 100. The retina faces the vitreous 12 and consists of two (2) basic layers: the neural retina and retinal pigment epithelium. The neural retina is the inner layer. It has nine (9) layers, including the photoreceptor layer. The retinal pigment epithelium is the outer layer that rests on Bruch's membrane and choroid.

The vitreous humor or vitreous 12 is the largest chamber of the eye (i.e. ~4.5 ml). The vitreous 12 is a viscous transparent gel composed mostly of water. The vitreous 12 also contains a random network of thin collagen fibers, mucopolysaccharides, and hyaluronic acid.

The vitreous 12 adheres firmly to the margin of the optic disc and to the peripheral retina at the ora serrata and the pars plana. With aging, the vitreous 12 liquefies, a process known as syneresis.

The aqueous humor 14 occupies the anterior chamber 18 of the eye 100. The aqueous humor 14 has a volume of about 0.6 mL and provides nutrients to the cornea 10 and lens 28. The aqueous humor 14 also maintains normal IOP.

As indicated above, the present invention provides improved agent delivery apparatus, systems and methods for administering a pharmacological agent formulation to a mucosa and/or sub-mucosal compartment of a body organ with the benefits of improved safety for the patient and increased efficiency for the practitioner. The agent delivery apparatus, in accordance with the present invention, is adapted to deliver pharmacological agent formulations, such as liquid agent formulations, to an organ's mucosa and/or sub-mucosal compartment by transmitting (or injecting) very fine streams of the agent formulations at high velocity.

According to the invention, the pharmacological agent formulations can comprise various forms, including, without limitation, solutions and suspensions.

The invention is also directed to an agent delivery assembly or kit, which, in one embodiment of the invention, includes (1) a pharmacological agent formulation, i.e. active agent formulation, containing an effective amount of an agent useful for treating a disorder associated with an organ; and (2)

injector means that is adapted to contain the pharmacological agent formulation and includes and an elongated agent delivery member, the injector means including force generating means that is adapted to generate sufficient force to expel the pharmacological agent formulation from the injector means and into and through the agent delivery member, and out of an ejection end of the elongated agent delivery member into the organ's sub-mucosal compartment.

In one embodiment of the invention, the injector means provides a delivery pressure in the range of approximately 50-1000 psi.

In one embodiment of the invention, the volume of the pharmacological agent formulation delivered to the sub-mucosal compartment is preferably in the range of approximately 0.025-1 mL.

Figure 2:
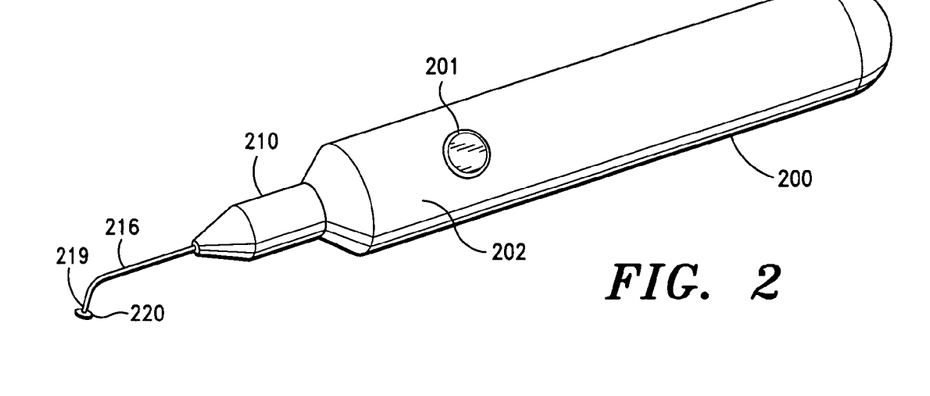
FIG. 2 is a perspective view of a agent delivery apparatus, in accordance with one embodiment of the invention.
Figure 3:
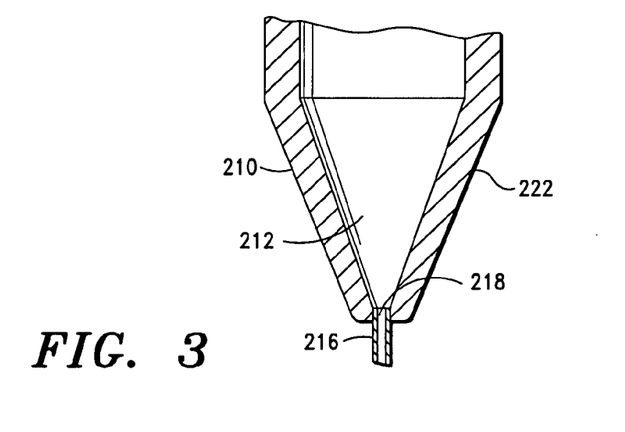
FIG. 3 is a partial sectional front plane view of an injector transfer mechanism, in accordance with one embodiment of the invention.

Referring now to FIG. 2, there is shown one embodiment of an agent delivery apparatus 200 of the invention. As illustrated in FIG. 2, the delivery apparatus 200 includes a jet injector 202, such as that disclosed in the '078 patent, a transfer member or mechanism 210 having an internal formulation chamber 212 that is adapted to receive a pharmacological agent formulation therein and an elongated agent delivery member 216. The delivery member 216 includes an opening (or lumen) 218 at the distal end that is in communication with the formulation chamber 212 (see FIG. 3) and a positioning hood 220 disposed proximate the ejection end 219.

According to the invention, the agent delivery member 216 is fabricated using a flexible material that would allow an operator to bend the delivery member 216 to a desirable orientation or arch to facilitate agent delivery to an organ's mucosa and/or its particular location. In some embodiments of the invention, the delivery member is thus fabricated from a suitable, preferably, biocompatible material such as silicon, polyurethane, polyethylene, hydrogel and like materials.

According to the invention, the delivery member 216 can have virtually any desired length. In some embodiments of the invention, the delivery member 216 has a length in the range of approximately 2-45 mm. In some embodiments of the invention, the delivery member 216 has a length in the range of approximately 1-50 cm.

In some embodiments of the invention, the delivery member 216 has an outer diameter in the range of approximately 20 microns to 3 mm.

In some embodiments of the invention, the delivery member 216 includes fiber optic and/or light transmitting and/or a micro-lens for providing direct monitoring of target organ and/or delivery process on a video screen.

In some embodiments, the injector 200 or delivery member 216 includes manual or automated means for adjusting the bend or configuration of the delivery member 216.

According to the invention, the delivery member can comprise a needleless delivery member or a microneedle delivery member to provide effective administration of pharmacological agent formulations to an organ's mucosa and/or sub-mucosal compartment.

Figure 4:
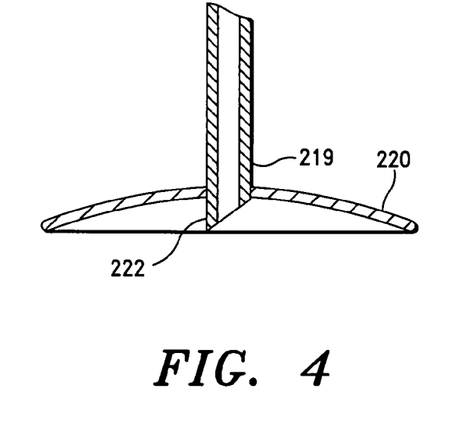
FIG. 4 is a partial sectional front plane view of a microneedle delivery member end, in accordance with one embodiment of the invention.

Referring now to FIG. 4, there is shown one embodiment of a microneedle delivery member end 219 having a microneedle 222 associated therewith. According to the invention, the microneedle 222 can have a penetrating length in the range of approximately 0.1-1 mm. The term "penetrating length" length refers to the actual length of the microneedle 222 that is allowed to penetrate the organ's tissue.

However, as will be readily appreciated by one having ordinary skill in the art, the length of the microneedle 222 can be readily modified, e.g., diameter, length, etc., to accommodate the sub-mucosal compartment delivery methods of the invention.

According to the invention, the microneedle 222 can be formed on the ejection end 219 of the delivery member 216, as shown in FIG. 4, or can comprise a separate integral component of the delivery member 216.

Figure 5:
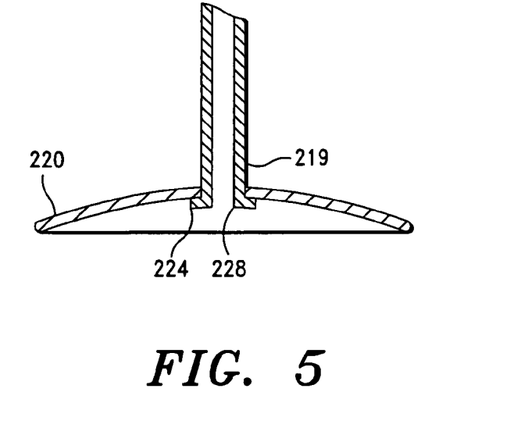
FIG. 5 is a partial sectional front plane view of a needleless delivery member end, in accordance with one embodiment of the invention.
Figure 6:
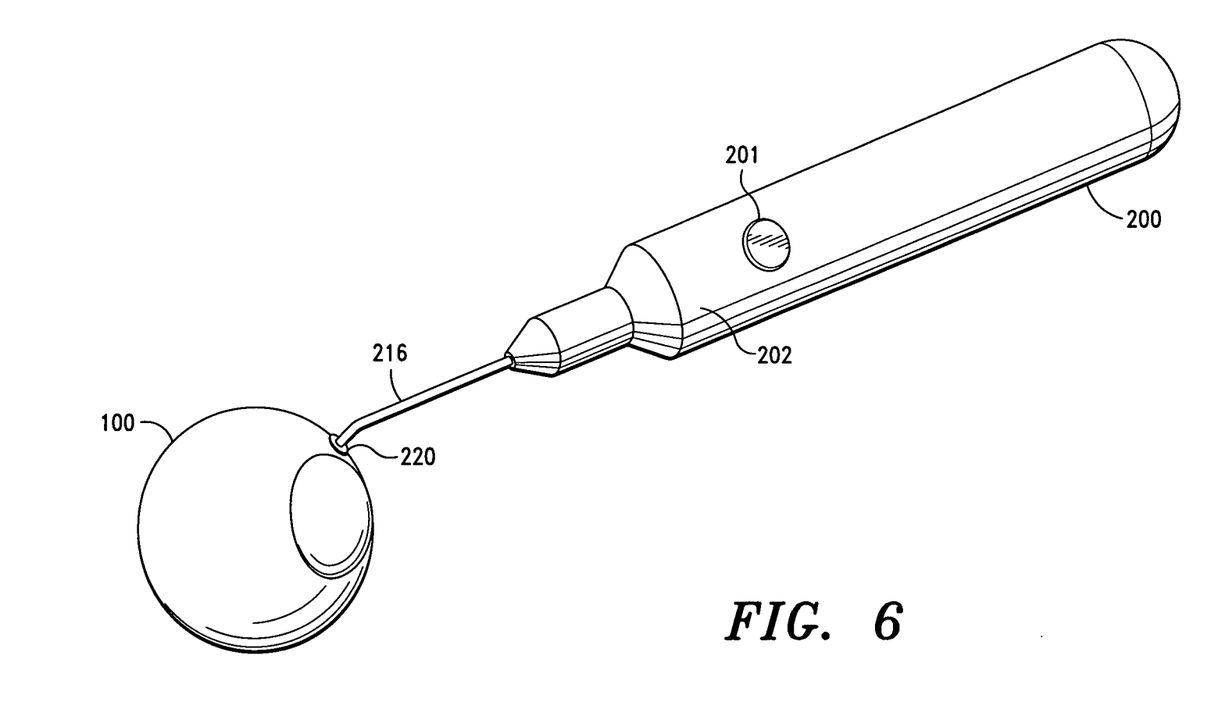
FIG. 6 is a perspective view of the agent delivery apparatus shown in FIG. 2 positioned on an eye, in accordance with one embodiment of the invention.

In a preferred embodiment of the invention, a needleless delivery member is employed to deliver a pharmacological agent formulation to the sub-mucosal compartment. Referring now to FIG. 5, there is shown one embodiment of a needleless delivery member end 219 having a delivery nozzle 224 associated therewith. As illustrated in FIG. 5, the nozzle 224 includes an internal lumen 226, which is adapted to receive and transfer pharmacological agent formulations therethrough, and flanged end 228.

Preferably, the internal lumen 226 has an internal diameter in the range of approximately 0.025 mm to 0.25 mm.

Referring back to FIG. 2, the transfer mechanism 210 is designed and adapted to be coupled to the jet injector 200. According to the invention, coupling of the transfer mechanism 210 and jet injector 200 can be achieved by providing external threads on the end of the transfer mechanism 210 that are adapted to cooperate with corresponding threads formed on the inner wall surface of the injector 200, as described in the '078 patent.

According to the invention, the jet injectors of the invention are preferably reusable and can be powered by compressed gas, pyrotechnics, electricity, or a spring, such as disclosed in U.S. Pat. Nos. 5,954,689, 5,704,911, 5,505,697, 6,585,685 and 7,150,409; which are incorporated by reference herein. In all cases, activation of the jet injector 200 is preferably accomplished by depressing an actuation button 201, which triggers the appropriate power source of the jet injector 200.

In an alternative embodiment of the invention, the jet injectors of the invention are disposable, as described, for example in U.S. Pat. No. 6,682,504; which is also incorporated by reference herein. The jet injectors can also be preassembled and ready for use without any further assembly.

In one embodiment of the invention, the jet injectors of the invention are capable of providing a delivery pressure in the range of approximately 50-1000 psi (measured as the force of a pharmacological agent formulation or fluid stream divided by the cross-sectional area of the fluid stream).

In one embodiment of the invention, the total volume of the pharmacological agent formulation administered to a sub-mucosal compartment is preferably in the range of approximately 0.025-2 mL.

As is well known in the art, use of a conventional needleless jet injector to administer agents is technically challenging. If the needleless jet injector is not positioned perpendicular to the tissue interface or if a poor contact is established between the nozzle and the tissue at the time of injection, a "wet" injection may occur. A wet injection is characterized by loss of a significant fraction of the medication at the surface of the tissue and/or, in the case of the skin, injection of the medication into the dermis instead of the subcutaneous or intramuscular space.

One of the root causes for wet injection is non-perpendicularity of the nozzle with the surface of the tissue with the result of the jet contacting the surface of the tissue at an angle. This can result in reflection of all or part of the jet by the tissue surface and/or total or partial intradermal injection.

Another cause for wet injection is poor contact with the tissue, which results in dissipation of a significant fraction of the jet energy through air aspiration that may be injected concomitantly with the medication.

Although wet injection is not desirable during transdermal administration, its consequences are relatively benign and a small percentage of such failure is generally deemed acceptable.

In the case of agent delivery to a sub-mucosal compartment of an eye, wet injection would result in significant loss of the medication at the surface of the conjunctiva, which could likely cause potential harmful consequences, depending of the agent being considered. Additional potential adverse consequences include air/contamination entrapment, potentially resulting in tissue damage, infection, and subsequent inflammation.

As will thus be readily appreciated by one having ordinary skill in the art, the use of an injector agent delivery member having a positioning hood that is adapted to position and, in some instances, secure the delivery member (and, hence, delivery apparatus associated therewith) to an eye structure, e.g., conjunctiva, or organ tissue prior to dispensing a pharmacological agent formulation, minimizes the risk of wet injection. Thus, in a preferred embodiment of the invention, as shown in FIG. 2, the injector delivery member 216 includes a positioning hood 220 to ensure desired positioning of the agent delivery apparatus to a surface of an eye structure, e.g. conjunctiva, or other organ thereby minimizing air entrapment and bacterial contamination.

According to the invention, the hood 220 can comprise various shapes, e.g., circular, kidney shaped, etc. In the illustrated embodiment, the hood 220 has a substantially circular shape.

In some aspects of the invention, the hood 220 comprises a positioning hood that is adapted to substantially conform to the surface of an organ and position the delivery member on the organ when in an engagement position thereon.

In some aspects of the invention, the hood 220 is further adapted to slightly retract when in contact with the organ's surface to permit positioning of the hood 220 in an angulated space.

In some aspects of the invention, the hood 220 comprises microneedle limiter means for limiting the penetration depth of a microneedle associated with a microneedle agent delivery member.

In some embodiments of the invention, the hood 220 includes suction means, such as those disclosed in the '078 patent. As set forth in the noted patent, the suction means provides an engagement force when the hood 220 is positioned on the surface or an organ or eye structure. Examples of suitable suction means include, without limitation, suction cups and suction rings.

As is well known in the art, needleless delivery of a pharmacological agent formulation to the eye typically requires a delivery pressure greater than approximately 4000 psi (measured as the force of the fluid stream divided by the cross-sectional area of the fluid stream) to penetrate all of the layers of the eye.

Applicants have, however, found that a delivery pressure of only approximately 50 to 1000 psi is required to effectuate pharmacological agent transfer through the mucosal layer and into a sub-mucosal compartment with a needleless agent delivery apparatus of the invention. Applicants further submit that the noted delivery pressure range offers the greatest safety for subconjunctival agent delivery.

Referring now to FIG. 5, there is shown an illustration of a delivery member of the invention, i.e. jet injector 200, positioned on an eye 100 to effectuate delivery of a pharmacological agent formulation to a sub-mucosal compartment of the eye 100.

According to the invention, the pharmacological agent formulation to be administered can be contained in the internal formulation chamber 212 of the injector 200, or, as set forth in the '078 patent, the pharmacological agent formulation can be contained in a disposable prefilled cartridge that is operatively receivable by the jet injector 200.

As illustrated in FIG. 5, in a preferred embodiment of the invention, to administer a pharmacological agent formulation to a sub-mucosal compartment of the eye 100, the distal surface of the delivery member hood 220 is initially positioned on the surface of the mucosal layer or conjunctiva 13. The activation button 201 is then depressed, whereby the injector 200 is activated and the agent formulation is expelled from the injector 200 and delivered to the sub-mucosal compartment of the eye 100.

As will readily be appreciated by one having ordinary skill in the art, the present invention provides numerous advantages compared to prior art methods and systems for administering agents and formulations thereof to subconjunctival compartment of the eye. Among the advantages are the following:

The provision of an agent delivery method and system that provides safe, accurate, consistent, and rapid delivery of therapeutic agents to mucosal tissue and/or into sub-mucosal compartments of organs.

The provision of an agent delivery method and system that facilitates delivery of therapeutic agents into the subconjunctival, retrobulbar, subtenon, intrascleral and subchoroidal compartments of the eye and/or behind the lid thereof with minimal risk of trauma and infection.

Without departing from the spirit and scope of this invention, one of ordinary skill can make various changes and modifications to the invention to adapt it to various usages and conditions. As such, these changes and modifications are properly, equitably, and intended to be, within the full scope and range of equivalence of the invention.

What is claimed is:

1. A method for administering a pharmacological agent formulation to a sub-mucosal compartment of an organ, comprising the steps of (i) providing a needleless agent delivery apparatus containing the pharmacological agent formulation in an internal formulation chamber, said agent delivery apparatus including an elongated agent delivery member, said agent delivery member including an integral nozzle member-positioning hood assembly, said nozzle member-positioning hood assembly comprising a first nozzle member and a deformable positioning hood that is adapted to substantially conform to the surface of an organ and position said agent delivery member on said organ when in an engagement position thereon, and force generating means that is adapted to generate sufficient force to expel the pharmacological agent formulation from said agent delivery apparatus and into an organ, (ii) positioning said agent delivery apparatus on a surface of a first organ, and (iii) activating the agent delivery apparatus, whereby the pharmacological agent formulation is expelled from the agent delivery apparatus by said force generating means and delivered to the surface of said first organ with a delivery pressure in the range of approximately 100-1000 psi and, whereby a first volume of the pharmacological agent formulation is administered to a sub-mucosal compartment of said first organ.

2. The method of claim 1, wherein said first volume of the pharmacological agent formulation administered to said sub-mucosal compartment of said first organ is in the range of approximately 0.025-1 ml.

3. The method of claim 1, wherein said first organ comprises the eye.

4. The method of claim 1, wherein said first organ comprises an organ selected from the group consisting of the nose, mouth, throat, trachea, esophagus, stomach, urethra, bladder and vagina.

5. The method of claim 1, wherein said agent delivery member includes suction means that provides an eye engagement force and seals said agent delivery member to said first organ when said delivery member is in said engagement position.

* * * * *